United States Patent
Kremeier

(10) Patent No.: US 12,303,244 B2
(45) Date of Patent: May 20, 2025

(54) SYSTEM FOR RECORDING THE BREATHING EFFORTS OF A PATIENT

(71) Applicant: Loewenstein Medical Technology S.A., Luxembourg (LU)

(72) Inventor: Peter Kremeier, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1878 days.

(21) Appl. No.: 16/260,358

(22) Filed: Jan. 29, 2019

(65) Prior Publication Data

US 2019/0231202 A1    Aug. 1, 2019

(30) Foreign Application Priority Data

Jan. 31, 2018  (DE) .......................... 102018000757.0

(51) Int. Cl.
| | |
|---|---|
| *A61B 5/03* | (2006.01) |
| *A61B 5/00* | (2006.01) |
| *A61B 5/08* | (2006.01) |
| *A61B 5/085* | (2006.01) |
| *A61B 5/087* | (2006.01) |

(Continued)

(52) U.S. Cl.
CPC .............. *A61B 5/036* (2013.01); *A61B 5/037* (2013.01); *A61B 5/0803* (2013.01); *A61B 5/085* (2013.01); *A61B 5/4836* (2013.01); *A61B 5/6853* (2013.01); *A61M 16/0003* (2014.02); *A61M 16/0051* (2013.01); *A61M 16/024* (2017.08); *A61M 16/044* (2013.01); *A61M 25/10* (2013.01); *A61M 25/1002* (2013.01); *A61M 25/10184* (2013.11); *G16H 20/00* (2018.01); *G16H 40/63* (2018.01); *A61B 5/0816* (2013.01); *A61B 5/087* (2013.01); *A61B 2562/0247* (2013.01); *A61J 15/0003* (2013.01); *A61J 15/0049* (2013.01); *A61J 15/0073* (2013.01); *A61J 15/0084* (2015.05); *A61M 2016/0027* (2013.01); *A61M 16/04* (2013.01); *A61M 16/0434* (2013.01); *A61M 2205/3334* (2013.01);

(Continued)

(58) Field of Classification Search
CPC ........ A61M 2016/0027; A61M 16/026; A61M 16/0003; A61M 2210/105; A61M 2016/0036; A61M 2205/3331; A61M 2230/005; A61M 16/0409
See application file for complete search history.

(56) References Cited

U.S. PATENT DOCUMENTS

| | | |
|---|---|---|
| 5,520,192 A | 5/1996 | Kitney |
| 2003/0000526 A1 | 1/2003 | Gobel |

(Continued)

FOREIGN PATENT DOCUMENTS

| | | |
|---|---|---|
| DE | 10213905 A1 | 10/2002 |
| DE | 102012215662 A1 | 3/2014 |
| EP | 2397074 A1 | 12/2011 |
| WO | 2006079152 A1 | 8/2006 |
| WO | 2010121313 A1 | 10/2010 |

*Primary Examiner* — Thaddeus B Cox
*Assistant Examiner* — Karen E Toth
(74) *Attorney, Agent, or Firm* — Abel Schillinger, LLP

(57) ABSTRACT

The invention relates to a system for recording breathing efforts of a patient, which comprises a pressure determination device for determining a transpulmonary pressure at the point in time of the breathing effort of the patient. The invention moreover relates to a unit for recording the optimum filling volume of the balloon of an esophageal catheter.

20 Claims, 7 Drawing Sheets

(51) Int. Cl.
*A61J 15/00* (2006.01)
*A61M 16/00* (2006.01)
*A61M 16/04* (2006.01)
*A61M 25/10* (2013.01)
*G16H 20/00* (2018.01)
*G16H 40/60* (2018.01)
*G16H 40/63* (2018.01)

(52) U.S. Cl.
CPC ............... *A61M 2205/3344* (2013.01); *A61M 2205/3553* (2013.01); *A61M 2205/3561* (2013.01); *A61M 2210/101* (2013.01); *A61M 2210/105* (2013.01); *A61M 2230/005* (2013.01); *A61M 2230/08* (2013.01); *A61M 2230/40* (2013.01); *A61M 2230/65* (2013.01); *G16H 40/60* (2018.01)

(56) References Cited

U.S. PATENT DOCUMENTS

| | | | |
|---|---|---|---|
| 2008/0110461 A1 | 5/2008 | Mulqueeny | |
| 2010/0228142 A1* | 9/2010 | Sinderby | A61M 16/026 600/533 |
| 2012/0037159 A1* | 2/2012 | Mulqueeny | A61B 5/091 128/204.23 |
| 2013/0174846 A1 | 7/2013 | Stenqvist | |
| 2015/0040905 A1* | 2/2015 | Kulstad | A61M 16/10 128/204.23 |
| 2015/0173634 A1* | 6/2015 | Pintel | A61B 5/033 600/587 |
| 2015/0217069 A1* | 8/2015 | Novotni | A61M 16/20 128/204.23 |
| 2016/0279361 A1 | 9/2016 | Mulqueeny | |
| 2018/0333552 A1* | 11/2018 | Göbel | A61M 29/02 |

\* cited by examiner

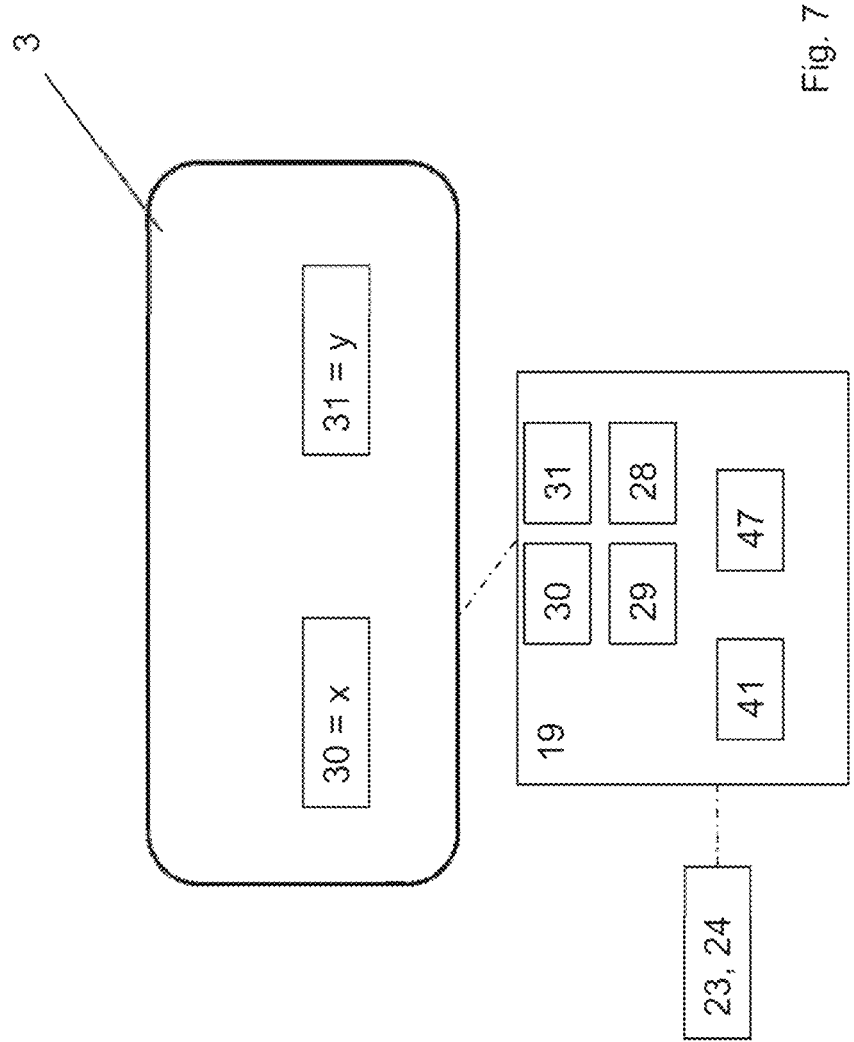

SYSTEM FOR RECORDING THE BREATHING EFFORTS OF A PATIENT

CROSS-REFERENCE TO RELATED APPLICATIONS

The present application claims priority under 35 U.S.C. § 119 of German Patent Application No. 102018000757.0 filed Jan. 31, 2018, the entire disclosure of which is expressly incorporated by reference herein.

BACKGROUND OF THE INVENTION

1. Field of the Invention

The present invention relates to a system for recording the breathing efforts of a patient.

2. Discussion of Background Information

Assisted respiration is assisting respiration. The respiration is triggered by a so-called trigger. The patient generates a respiratory gas flow or pressure themselves at the beginning of inhalation, which the respirator recognizes as a trigger. If the trigger generated by the patient exceeds the preset threshold, i.e., the set trigger level, the respirator thus supplies respiratory gas at a specific pressure and/or volume and thus facilitates the breath.

The goal of assisted respiration in this case is to adapt the insufflation by the respirator to the breathing efforts of the patient, to thus optimize patient comfort and minimize breathing work. An asynchronicity between the patient and the respirator, which is defined as a discrepancy between the natural inspiration time of the patient and the insufflation time of the respirator, is a frequent phenomenon in clinical practice. Almost a quarter of intubated patients display substantial asynchronicities during assisted mechanical respiration, which are often not clinically recognized. The most frequent asynchronicity patterns are ineffective triggers, in which the inspiration efforts of the patient do not trigger a respiration stroke, since, at the time the attempt is made to trigger the trigger, dynamic hyperinflation exists.

An asynchronicity can be, on the one hand, an indication of the severity of the respiratory status, however, it can also be linked to unsuitable settings of the respirator, which lengthen the duration of the mechanical respiration. Various settings which are to improve the synchronicity by reducing the dynamic hyperinflation have already been proposed, for example the application of an external positive end-expiratory pressure (PEEP) and the reduction of the insufflation time or the avoidance of an inadequately high pressure assistance. These approaches have heretofore not been systematically compared, however, and the respective effects thereof on the breathing work and the tidal volume thus remain unclear.

SUMMARY OF THE INVENTION

The invention provides a system for recording the breathing efforts of a patient, which comprises a pressure determination device for determining a pressure at the point in time of the breathing effort of the patient.

In this case, the breathing effort can be an active (muscular) or a passive (for example, restoring forces) breathing effort.

The system can also be characterized in that the point in time of the breathing effort is the beginning of the expiration or the beginning of the inspiration of the patient.

The system can also be characterized in that the pressure determination device is designed as an esophageal catheter and has a gas-filled balloon.

The system can also be characterized in that the sensor of the respirator determines the esophageal pressure, which is recorded via the gas-filled balloon of the esophageal catheter.

The system can alternatively or additionally be designed for recording breathing efforts of a patient, comprising a pressure determination device, for determining a pressure at the point in time of the breathing effort of the patient, characterized in that the pressure determination device is designed as an esophageal catheter and has a gas-filled balloon, and comprising a respirator having a pressure inlet nozzle for the esophageal catheter and a pressure sensor, wherein a breathing effort of the patient is recorded via the gas-filled balloon of the esophageal catheter.

The system can alternatively or additionally be characterized in that the transpulmonary pressure is determined by the respirator in consideration of the respiratory pressure predetermined by the respirator and of the esophageal pressure determined by the sensor.

The system can alternatively or additionally be characterized in that the gas-filled balloon has a sensor, which registers a breathing effort and transmits it to a respirator.

The system can alternatively or additionally also be characterized in that the determination of the transpulmonary pressure takes place at the end of the exhalation TPP ex and/or at the end of the inhalation TPP in by way of a specific measuring procedure, in which the respirator prevents a respiratory gas transportation to or from the patient.

The system can alternatively or additionally also be characterized in that a breathing effort of the patient is compared to at least one stored threshold value and corresponds to a trigger upon exceeding the threshold value.

The system can alternatively or additionally also be characterized in that the point in time is the beginning of the expiration or the beginning of the inspiration of the patient.

The system can alternatively or additionally also be characterized in that the pressure determination device determines the esophageal pressure progressively, for example also at the beginning of the inspiration or the expiration.

The system can alternatively or additionally also be characterized in that the system moreover comprises a unit, for example a control unit, which specifies the respiratory gas pressure provided by the respirator in consideration of the determined esophageal pressure or transpulmonary pressure.

The system can alternatively or additionally also be characterized in that if the esophageal pressure exceeds or falls below a threshold value, the unit generates a control signal for the respirator to specify an inspiratory or expiratory respiratory gas pressure.

The system can alternatively or additionally also be characterized in that the control unit of the respirator provides respiratory gas parameters (pressure, flow, volume, frequency) for a controlled or assisted respiration and controls the respiratory gas source to specify the controlled or assisted respiration.

The system can alternatively or additionally also be characterized in that the number of inspiration efforts of the patient per unit of time is recognized and recorded from the esophageal pressure curve.

The system can alternatively or additionally also be characterized in that the number of predetermined inspirations per unit of time is recognized and recorded from the respiratory pressure curve or the control unit.

The system can alternatively or additionally also be characterized in that the inspiration efforts of the patient per unit of time are compared to the predetermined inspirations per unit of time and the degree of the synchronization between the inspiration efforts of the patient and the inspiration specification of the respirator is thus determined.

The system can alternatively or additionally also be characterized in that an index of the failed triggers is taken from this comparison, which index represents the degree of the synchronization between the inspiration efforts of the patient and the inspiration specification of the respirator.

The system can alternatively or additionally also be characterized in that the unit for recording the synchronicity recognizes failed triggers from the time interval between the predetermined respiratory gas stroke and the breathing effort of the patient and determines a failed trigger rate or an index and stores or displays it.

The system can alternatively or additionally also be characterized in that the unit for recording the synchronicity recognizes failed triggers from the time interval between the predetermined respiratory gas stroke and the breathing effort of the patient if the time interval is greater than $1/100$ of a second, preferably greater than $1/10$ of a second, particularly preferably greater than 1 second.

The system for recording breathing efforts of a patient can alternatively or additionally comprise a pressure determination device for determining a pressure at the point in time of the breathing effort of the patient, wherein the pressure determination device is designed as an esophageal catheter and has a gas-filled balloon and comprising a respirator having a pressure inlet nozzle for the esophageal catheter and a pressure sensor, wherein a breathing effort of the patient is recorded via the gas-filled balloon of the esophageal catheter, wherein the system moreover comprises a unit for recording the synchronicity of a respiratory gas stroke (pressure or volume or flow) predetermined (with respect to time) by the respirator with the breathing effort of the patient, wherein an index of the failed triggers is taken from this comparison, which index represents the degree of the synchronization between the inspiration efforts of the patient and the inspiration specification of the respirator.

The system can alternatively or additionally also be characterized in that the unit generates a control signal for the respirator to specify a changed inhalation time and/or a changed PEEP and/or a changed trigger sensitivity if failed triggers are recognized.

The system can alternatively or additionally also be characterized in that the esophageal catheter determines the functional positive end-expiratory pressure, which is referred to as intrinsic PEEP (PEEPi).

The system can alternatively or additionally also be characterized in that if the PEEPi exceeds or falls below a threshold value, the unit generates a control signal for the respirator to specify a changed respiratory gas volume or a changed exhalation time.

The system can alternatively or additionally also be characterized in that it comprises a unit for recording the optimum filling volume of the balloon, wherein the unit determines the smallest filling volume which makes up the greatest pulse pressure variation ("swing") of the balloon in one breath (from inspiratory to expiratory). The unit for recording the optimum filling volume of the balloon can be a flow or volume sensor which is for example arranged in the respirator and is connected to the control unit.

The invention also provides a system having a unit for recording the optimum filling volume of the balloon, wherein the unit determines the filling volume which makes up the greatest pulse pressure variation ("swing") of the balloon in one breath (from inspiratory to expiratory).

BRIEF DESCRIPTION OF THE DRAWINGS

Further advantages and features of the present invention result from the description of the exemplary embodiments, which are explained hereafter with reference to the appended figures.

In the figures:

FIG. 7 illustrates the determination of a failed trigger rate.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
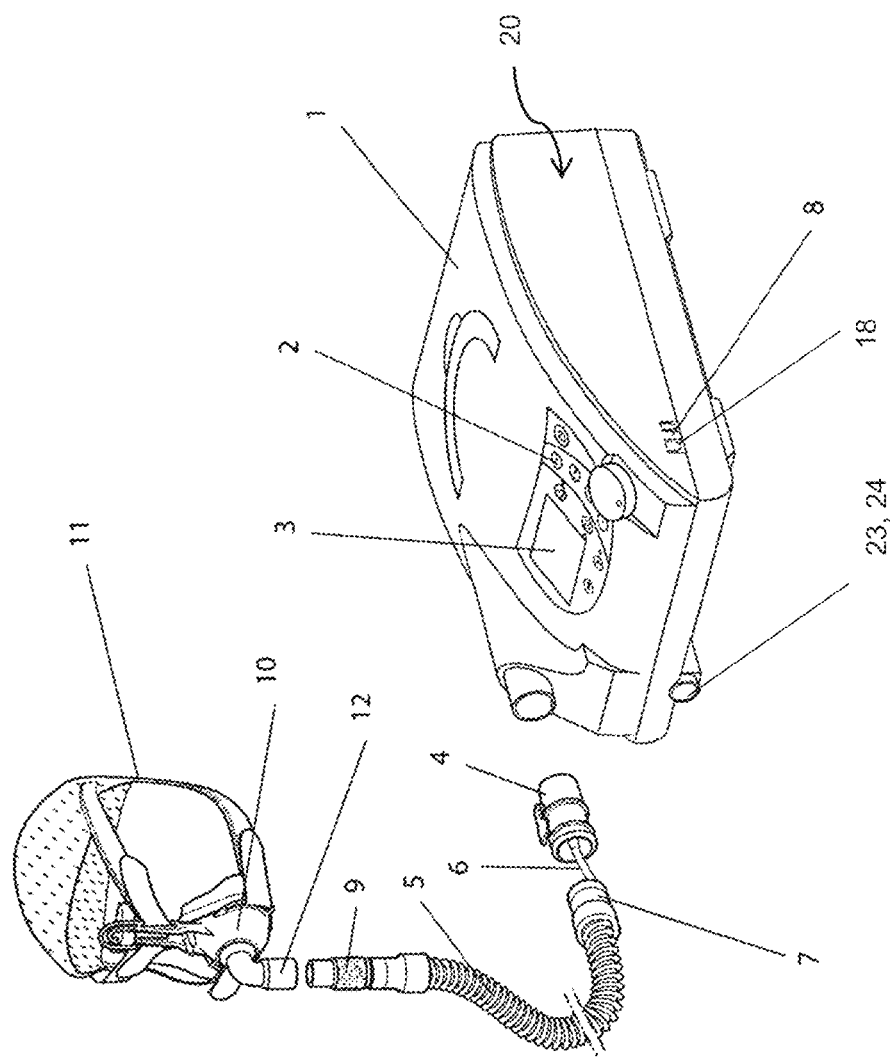
FIG. 1 shows the fundamental construction of a device for respiration.

FIG. 1 shows the fundamental construction of a respirator (20). An operating element (2) and/or an operating and information system (3) are arranged in the region of a device housing (1). A connecting hose (5) is connected via a coupling (4). An additional pressure measuring hose (6), which is connectable via a pressure inlet nozzle (7) to the device housing (1), can extend along the connecting hose (5). To enable data transfer, the device housing (1) has at least one interface (8, 18). A humidifier (21) or a nebulizer (22) can moreover be adapted. The respirator has a respiratory gas source (17).

An exhalation element (9) is arranged, for example, in the region of an extension of the connecting hose (5) facing away from the device housing (1). An exhalation valve can also be used.

The respirator (20) can be designed as a sleep therapy device, as a high-flow device, as an anesthesia device, as a clinical or home or emergency respirator.

FIG. 1 additionally shows a patient interface designed as a respiration mask (10). A fixation in the region of the head of a patient can be performed via headgear (11). The patient interface (10) has a coupling element (12) in the region of its extension facing toward the connecting hose (5). The patient interface can also be designed, for example, as a tube.

The input and/or output of data, for example dead space volume, can take place via the interface (8, 18). The interfaces can be implemented as wired, as an infrared interface, as a Bluetooth interface, or as USB. A card slot is preferably also provided. The interface (8) can also be embodied as a LAN interface or as another interface for connection to the Internet. An oxygen supply valve can be adapted to the device for respiration in the region of a device housing. It is conceivable to additionally enrich the respiratory gas with oxygen to improve the patient supply.

The respirator (20) according to the invention is designed in such a way that it can be connected via a hose and a patient interface to a patient in order to provide respiration. It comprises a source for respiratory gas (17), which is designed, for example, as an electric motor having a fan wheel or as a compressed gas fitting having at least one valve. The respirator has a unit for determining pressure and/or flow and/or volume of the respiratory gas. A control unit (19) is designed in such a way that, for example for each breath cycle on the basis of a predetermined value and/or on the basis of measurement signals for the parameters pressure and/or flow and/or volume, it determines a respiratory gas parameter and regulates the source for respiratory gas in such a way that the respiratory gas parameter is applied. The control unit can specify the parameters of the respiration in a monitored manner and/or at least partially in an assisted or adaptive manner in consideration of measurement signals.

The control unit (19) is designed, for example, in such a way that it determines the present pressure and/or flow and/or the volume of respiratory gas and displays the current value via the operating and information system connected to the control unit or the display (3). The control unit (19) is additionally designed in such a way that it determines trend changes of the computations thereof over time with respect to one or more parameters, wherein the trend changes can be displayed on the display.

Furthermore, the control unit (19) compares those parameter values which were specified by a user, for example upper and lower pressure limits or a maximum tolerable number of apneas per unit of time, or a maximum tolerable leakage, to the present values and generates a piece of user information for deviations from the specification. The user information is preferably graphically visualized via the operating and information system (3).

The control unit (19) is also designed, for example, so that it determines the esophageal pressure at least at times or in phases. The respirator (20) has for this purpose a (pneumatic or electronic or optical) pressure measuring input and a pressure sensor (23, 24), to which an esophageal balloon (62) is at least indirectly connected.

The control unit (19) is configured and designed, for example, to identify a change of the esophageal pressure and thereupon to control the respirator to specify a respiration parameter.

If the esophageal pressure (60) exceeds or falls below a threshold value, the control unit (19) generates, for example, a control signal for the respirator (20), to specify an inspiratory or expiratory respiratory gas pressure. If the esophageal pressure (60) exceeds or falls below a threshold value, the control unit (19) alternatively generates, for example, a control signal for the respirator (20), to end the specification of an inspiratory or expiratory respiratory gas pressure.

Figure 2:
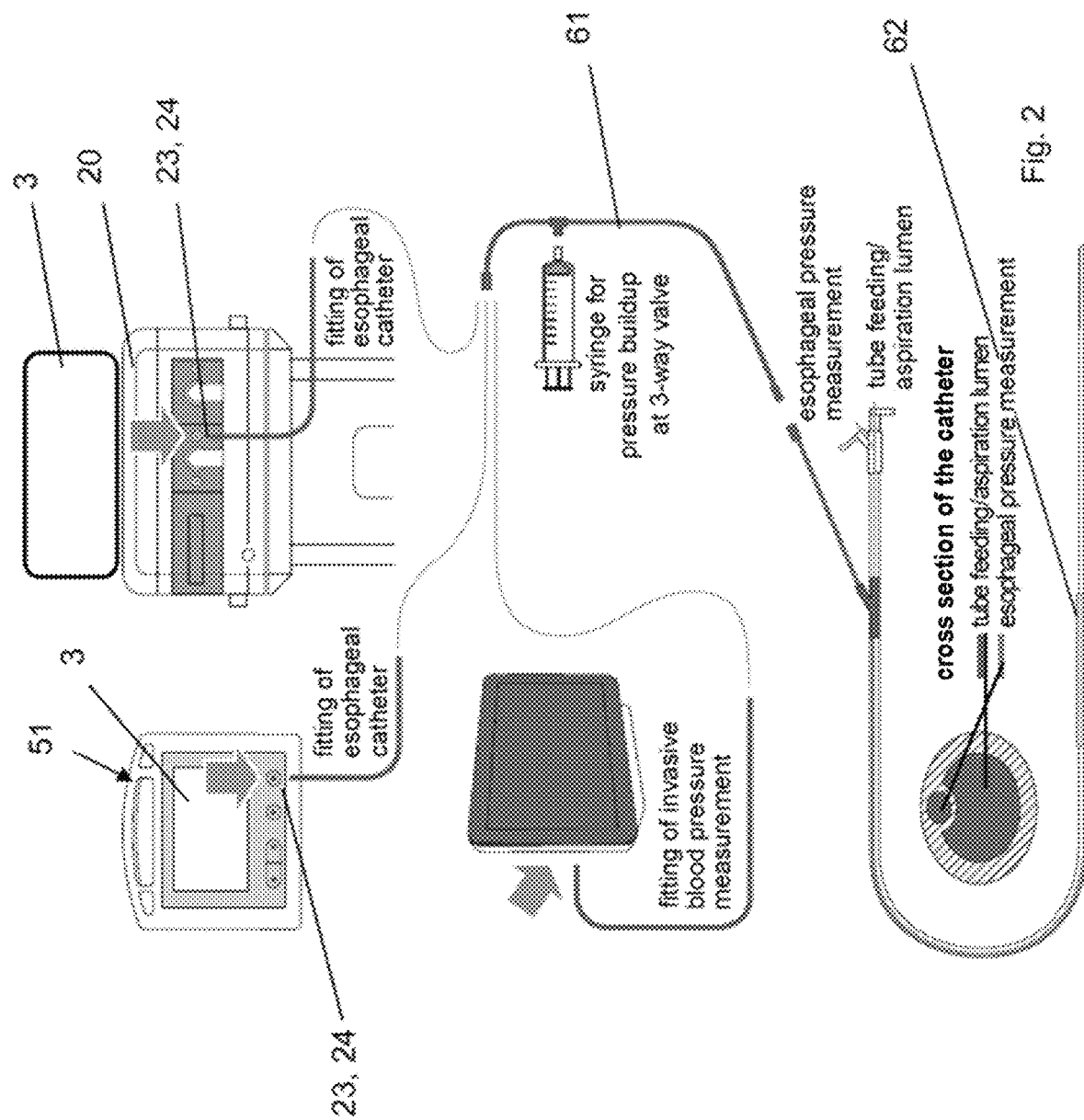
FIG. 2 schematically shows the arrangement of the respirator in the system according to the invention.

FIG. 2 schematically shows the arrangement of the respirator (20) in the system. The bedside measurement of the esophageal pressure (60, Peso) is based on the use of an esophageal balloon (62) and in this case reflects the changes of the pleural pressure (63) as a surrogate parameter. The transpulmonary pressures (64) measured or determined progressively or in phases enable the mechanical pressure and volume load under respiration to be evaluated and the respiration to be adapted accordingly to protect the lungs. The transpulmonary pressure (64) is determined or ascertained by computer for this purpose from the measured esophageal pressure (60, Peso) and the respiration pressure (27) specified or measured by the respirator (20). Only the measurement of the esophageal pressure (60, Peso) enables the determination of the transpulmonary pressure (64). This is the pressure which is required for the expansion of the lungs and the chest wall.

The transpulmonary pressure (64) corresponds to the pressure difference between the alveoli and the esophagus. For example, the transpulmonary pressure (64) can be measured at end-inspiratory or end-expiratory occlusion.

The system for recording breathing efforts of a patient (40) therefore comprises a pressure determination device, which is designed as an esophageal catheter (61), for determining a transpulmonary pressure (64) using, for example, end-inspiratory or end-expiratory occlusion maneuvers.

The esophageal catheter (61) has an air-filled balloon (62), which is used as a pressure pickup. The respirator (20) has a pressure inlet nozzle (23) for the esophageal catheter (61) and a corresponding pressure sensor (24), which determines the esophageal pressure (60, Peso).

Alternatively or additionally, the esophageal catheter (61) can be connected to a separate monitor (51). The monitor has for this purpose a (pneumatic or electronic or optical) pressure measuring input and a pressure sensor (23, 24), to which an esophageal balloon (62) is at least indirectly connected via the esophageal catheter (61). The monitor (51) and/or the respirator (3) can display and record the pressure curve of the transpulmonary pressure (64) and/or esophageal pressure (60, Peso) and/or of the respiration pressure (27).

In the simplest case, the esophageal catheter (61) has at least one lumen for the pressure measurement and an esophageal balloon (62). The esophageal catheter (61) can alternatively or additionally be embodied having multiple lumens and thus moreover enable tube feeding. Optionally, a blood pressure measurement and/or temperature measurement can additionally be added.

Figure 3:
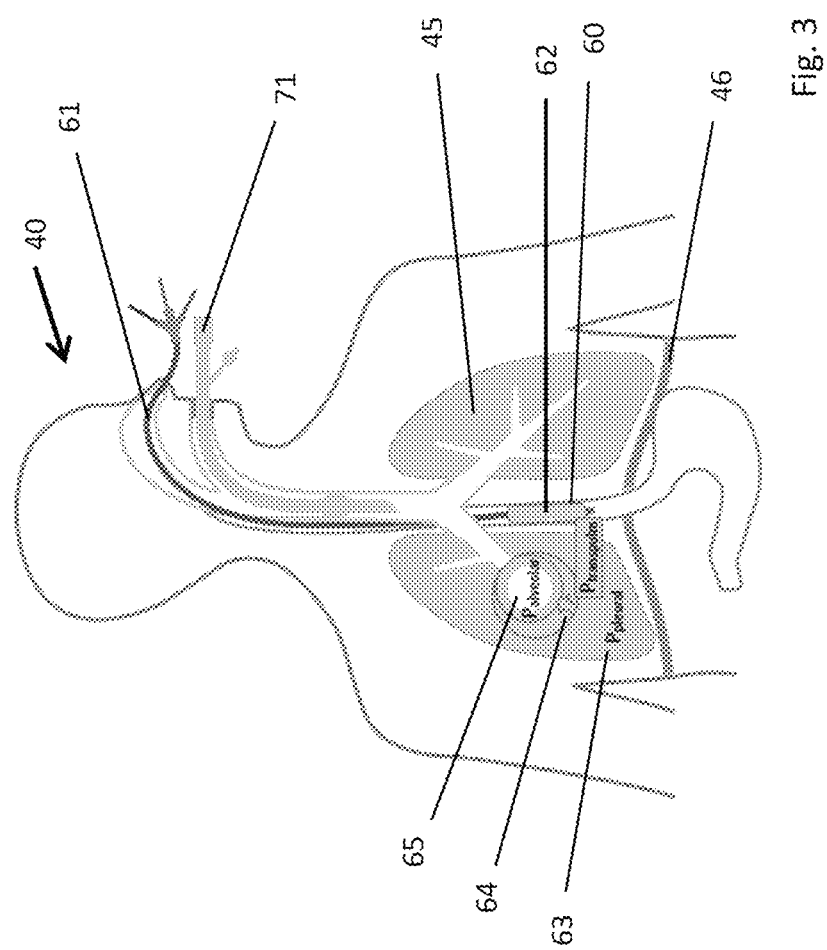
FIG. 3 schematically shows the arrangement of the system according to the invention in the patient.

FIG. 3 schematically shows the arrangement of the system in the patient. The system for recording breathing efforts of a patient (40) comprises a pressure determination device, which is designed as an esophageal catheter (61), for determining a transpulmonary pressure (64). This is equal in good approximation to the alveolar pressure. The transpulmonary pressure is determined from the respiration pressure (27) (specified by the respirator) and the Peso (60). The measurement and determination take place, for example, at the end of the exhalation (64 TPP ex) and/or at the end of the inhalation (64 TPP in) by way of a specific measuring procedure.

The esophageal catheter (61) has an air-filled balloon (62), which is used as a pressure pickup. The balloon section is located adjacent to the lungs in this case. A respiration tube (71) can be placed in the airways to respirate the patient. The two lungs (45) and the diaphragm (46) are visible.

Figure 4:
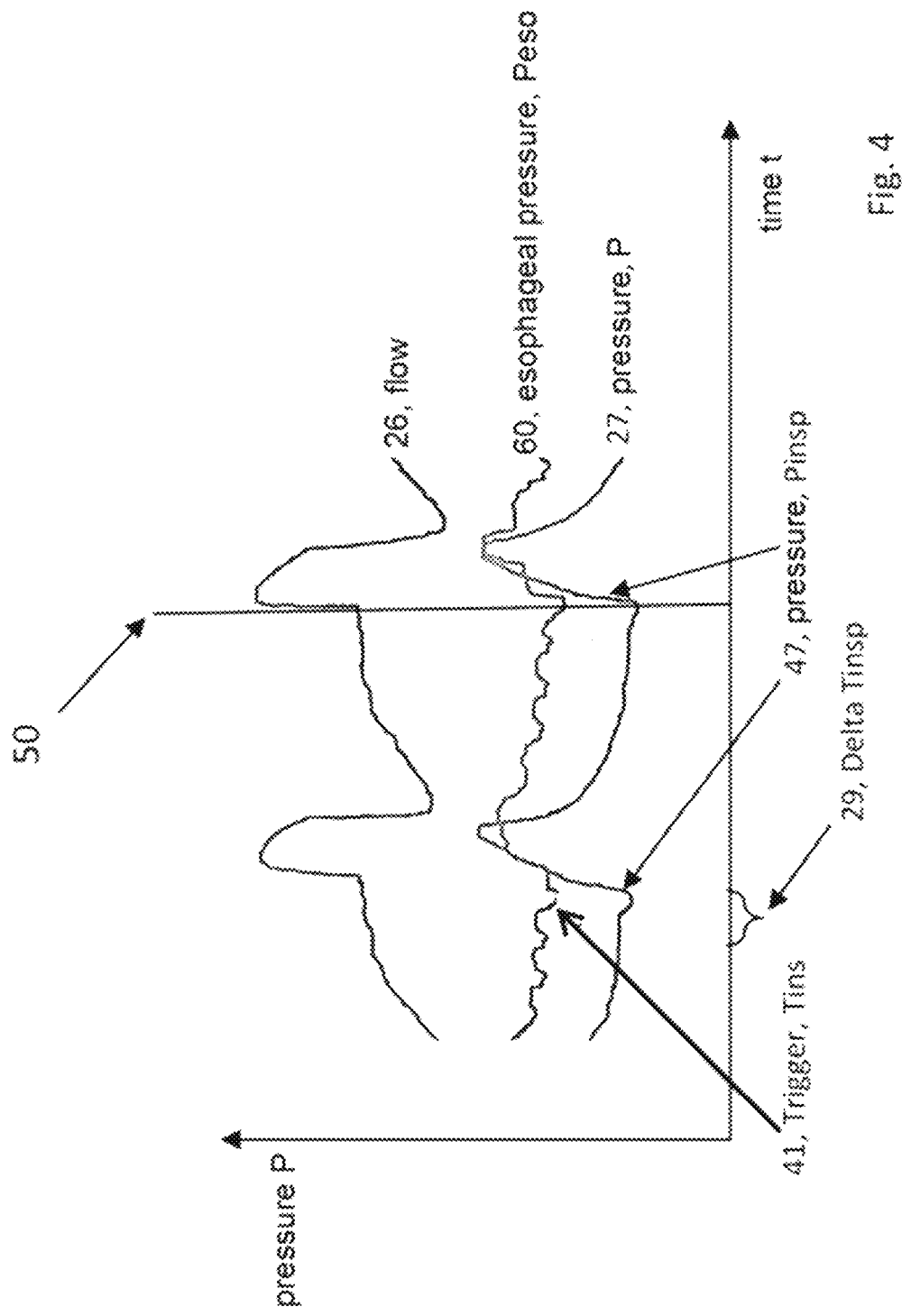
FIG. 4 schematically shows the curve of the signals flow (26), esophageal pressure (60), and respiration pressure (27)

FIG. 4 schematically shows the curve of the signals flow (26), esophageal pressure (60), and respiration pressure (27). It can be seen from the curve of the signals that the pressure determination device determines the esophageal pressure (60). A breathing effort of the patient (41) is recognized as a deflection in the esophageal pressure signal. Diaphragm contractions thus generate, for example, a negative Peso pressure (at 41). This patient trigger (41), in the left part of FIG. 4, is not recognized by the respirator as a trigger for the inspiration pressure increase (47). This becomes clear due to the time difference (29) between the patient trigger (41) and the actual inspiration pressure increase (47) by the respirator. According to the invention, this time difference (29) between the patient trigger (41) and the actual inspiration pressure increase (47) by the respirator can be recognized and analyzed to depict an asynchronicity (30) between the patient and the respirator, for example as an index of unsuccessful patient triggers (41).

According to the invention, it is also intended that a breathing effort of the patient (41) be recognized as a deflection in the esophageal pressure signal. Diaphragm contractions thus generate, for example, a negative Peso pressure (at 41). This patient trigger (41) is recognized, in the right part of FIG. 4, at the point in time (50) by the respirator as a trigger for the inspiratory pressure increase (47). The unit (19, control unit) for specifying the respiratory gas pressure has recognized here that the esophageal pressure (60) exceeds or falls below a threshold value and generates a control signal for the respirator (20) to specify an inspiration respiratory gas pressure (47). The inspiration respiratory gas pressure (47) results in a respiratory gas flow (26) to the patient.

With the esophageal pressure measurement, a measuring method is available which can unmask a patient-respirator asynchronicity. The monitoring of the esophageal pressure (60) helps in the recognition and treatment of the causes of the ineffective patient efforts (41). Diaphragm contractions generate a negative Peso pressure, which is not followed by an inspiration reaction in the respiration pressure curve. This problem configuration occurs more frequently due to the combination of high respiratory drive, high flow rate, and low tidal volume. Bedside monitoring of the breathing muscle activity in real time by means of esophageal pressure enables the degree of the synchronization (30) between the inspiration efforts of the patient and the insufflation time of the respirator to be evaluated and the respiration parameters (for example optimization of the insufflation time or of the pressure assistance, and/or of the PEEP) or the trigger sensitivity to be adapted accordingly.

A triggered respiration can avoid a diaphragm dysfunction by enabling the patient to generate spontaneous inspiration efforts. The goal of assisted respiration in this case is to adapt the insufflation by the respirator (47) to the breathing efforts of the patient (41) to thus optimize patient comfort and minimize breathing work. An asynchronicity (30) between the patient and the respirator, which is defined as a discrepancy between the natural inspiration time of the patient and the insufflation time of the respirator, is a frequent phenomenon in clinical practice. Almost a quarter of intubated patients display substantial asynchronicities during assisted mechanical respiration, which are often not clinically recognized. The most frequent asynchronicity patterns are ineffective triggers (41), in which the inspiration efforts of the patient do not trigger a respiration stroke, since, at the point in time at which an attempt is made to trigger the trigger, a dynamic hyperinflation exists, for example.

An asynchronicity (29) can be, on the one hand, an indication of the severity of the respiratory status, however, on the other hand, it can also be linked to unsuitable settings of the respirator, which extend the duration of the mechanical respiration. Various settings which are supposed to improve the synchronicity by reducing the dynamic hyperinflation have already been proposed, for example the application of an external positive end-expiratory pressure (PEEP) and the reduction of the insufflation time or the avoidance of an inadequately high pressure assistance. However, these approaches have heretofore not yet been systematically compared, and the respective effects thereof on the breathing work and the tidal volume thus remain unclear. A measurement method which can unmask a patient-respirator asynchronicity is available with the esophageal pressure measurement. The monitoring of the esophageal pressure helps in the recognition and treatment of the causes of the ineffective patient efforts. Because this asynchronicity is linked to an extended duration of the mechanical respiration, this could potentially have an effect on the duration of the machine respiration. Diaphragm contractions generate a negative Peso pressure, which is not followed by an inspiratory reaction in the respiration pressure curve. This problem constellation occurs more frequently due to the combination of high breathing work, high flow rate, and low tidal volume. Bedside monitoring of the breathing muscle activity in real time by means of esophageal pressure enables the degree of the synchronization between the inspiration efforts of the patient and the insufflation time of the respirator to be evaluated and the respiration parameters (for example optimization of the insufflation time or of the pressure assistance, and/or of the PEEP) to be adapted accordingly, for example, automatically.

The number of inspiration efforts (41) of the patient per unit of time is recognized and recorded from the esophageal pressure curve (60).

Moreover, the number of specified inspirations (47) per unit of time is recognized and recorded from the respiration pressure curve (27) or the control unit.

If the inspiration efforts of the patient (41) per unit of time are compared to the specified inspirations (47) per unit of time, the degree of the synchronization (30) between the inspiration efforts (41) of the patient and of the inspiration specification of the respirator can be determined.

According to the invention, an index (30) of the failed triggers can be inferred from this comparison, which represents the degree of the synchronization (30) between the inspiration efforts of the patient and the inspiration specification of the respirator.

TABLE 1

Unmasking of patient-respirator asynchronicity

| Case scenario | Clinical significance | Clinical recommendation |
|---|---|---|
| No Peso pressure negation before the pressure delivery by the respirator in spontaneously breathing patients | Auto-triggering | Checking & possibly adaptation: leaks trigger settings condensate in the hoses hose systems & respiration equipment having high resistance sedation depth |
| Peso pressure negation without pressure delivery by the respirator in spontaneously breathing patients | Asynchronicity | Checking & possibly adaptation: leaks trigger settings pressure increase speed ("ramp") inspiratory termination ("flow shutdown criterion") PEEP condensate in the hoses hose systems & respiration equipment having high resistance |

TABLE 1-continued

Unmasking of patient-respirator asynchronicity

| Case scenario | Clinical significance | Clinical recommendation |
|---|---|---|
| Peso inspiration time longer than inspiration time of the respirator | Double triggering or premature end of the inspiration phase | Checking & possibly adaptation: inspiration time of respirator level and nature of the pressure assistance metabolic acidosis encephalopathy |
| Periodically occurring Peso negation after the delivery of mandatory breaths | Recognition of "reverse triggering" | Reduce or change sedation (inadequate sedation depth) |

Figure 5:
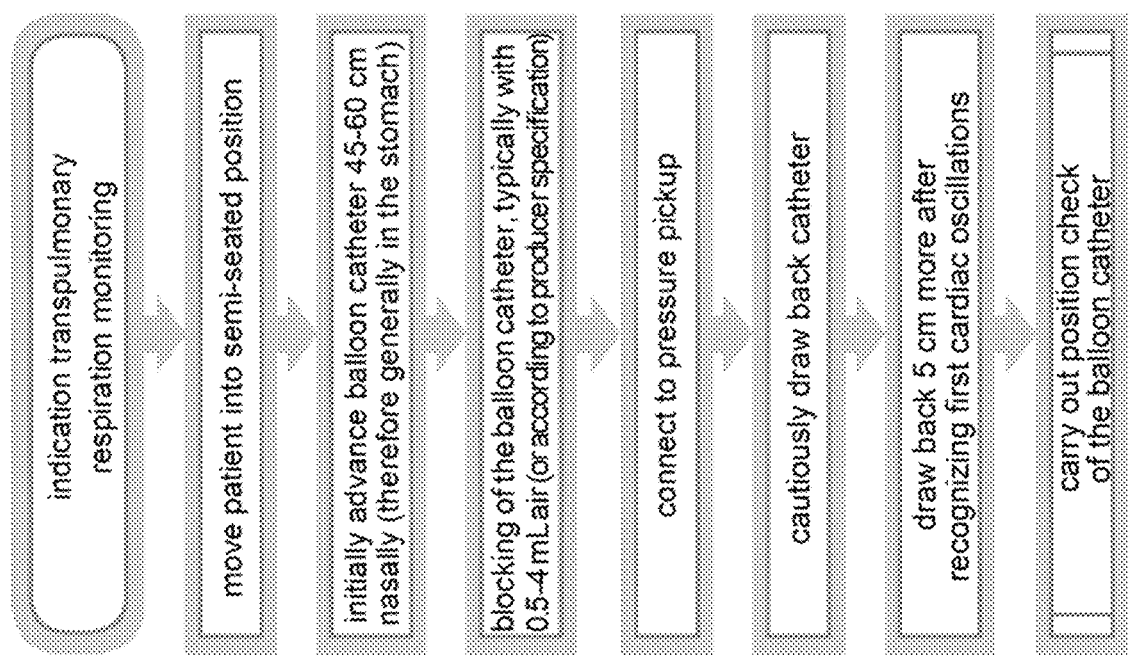
FIG. 5 shows the placement of a Peso catheter.

FIG. 5 shows the placement of the Peso catheter. With test subjects seated upright, the pleural pressure (63) was estimated by measuring the esophageal pressure using an esophageal balloon catheter. The Peso changes during the breathing cycle reflect the changes of the pleural pressure (63) acting on the lung surface. The difference between respiration pressure and esophageal pressure is a valid estimation of the transpulmonary pressure (64, TPP) in the region around the balloon catheter. Absolute values of Peso can be influenced by the breathing mechanism, the lung volume, the weight of the mediastinum, the abdomen, the posture, the reactivity of the smooth muscle wall, and the mechanical properties of the balloon.

The present state of knowledge about the effect of the position of the patient on the observed esophageal pressure and his respiratory variation in the case of special lung and chest wall illnesses and pleural effusions is still limited. In manifold studies, however, it has been possible to show that even under these conditions, the esophageal pressure represents an acceptable, expedient, and suitable surrogate parameter to the pleural pressure (63). For the Peso measuring method, which has become the most frequently used in the meantime, an air- or gas-filled esophageal balloon, more or less a modified stomach probe, is used, which is connected via a long, thin catheter to a pressure pickup. Esophageal catheters can be connected to modern intensive ventilators (20) using corresponding fittings (23, 24), to special monitors (51) for esophageal pressure measurement, or to the invasive RR measurement of intensive monitoring monitors.

To obtain a reliable Peso measurement, the esophageal balloon has to be located at a suitable position and be filled with a sufficient air volume. The Peso will not be correctly transferred if the balloon is underfilled. However, an overfilled balloon can also result in overestimation of the pressure. The air volume which is "optimal" for the filling is dependent on design, dimensions, geometry, and material of the esophageal balloon, which in turn have effects on its mechanical properties. The six most widespread commercially available esophageal catheters have been tested in vitro at external pressures of 0 to 30 cm H2O. It was shown in this case that all studied catheters correctly measured the ambient pressure, but significant differences existed in the optimum filling volume between the catheters.

Moreover, the minimum volume required for usable measurements was greater than previously recommended and was additionally dependent on the ambient pressure. A further study also showed that the filling volume was different for the various catheters examined, and that at high pressures a greater filling volume was necessary. In clinical practice, the optimum filling volume may be easily determined, for example, by gradually filling the balloon in the range provided for the respective catheter and thus determining the smallest volume at which the coarsest pulse pressure variation ("swing") of the Peso occurs in one breath (from inspiratory to expiratory). Peso monitoring monitors and intensive ventilators according to the invention have special algorithms for optimum filling of the catheter balloon.

Figure 6:
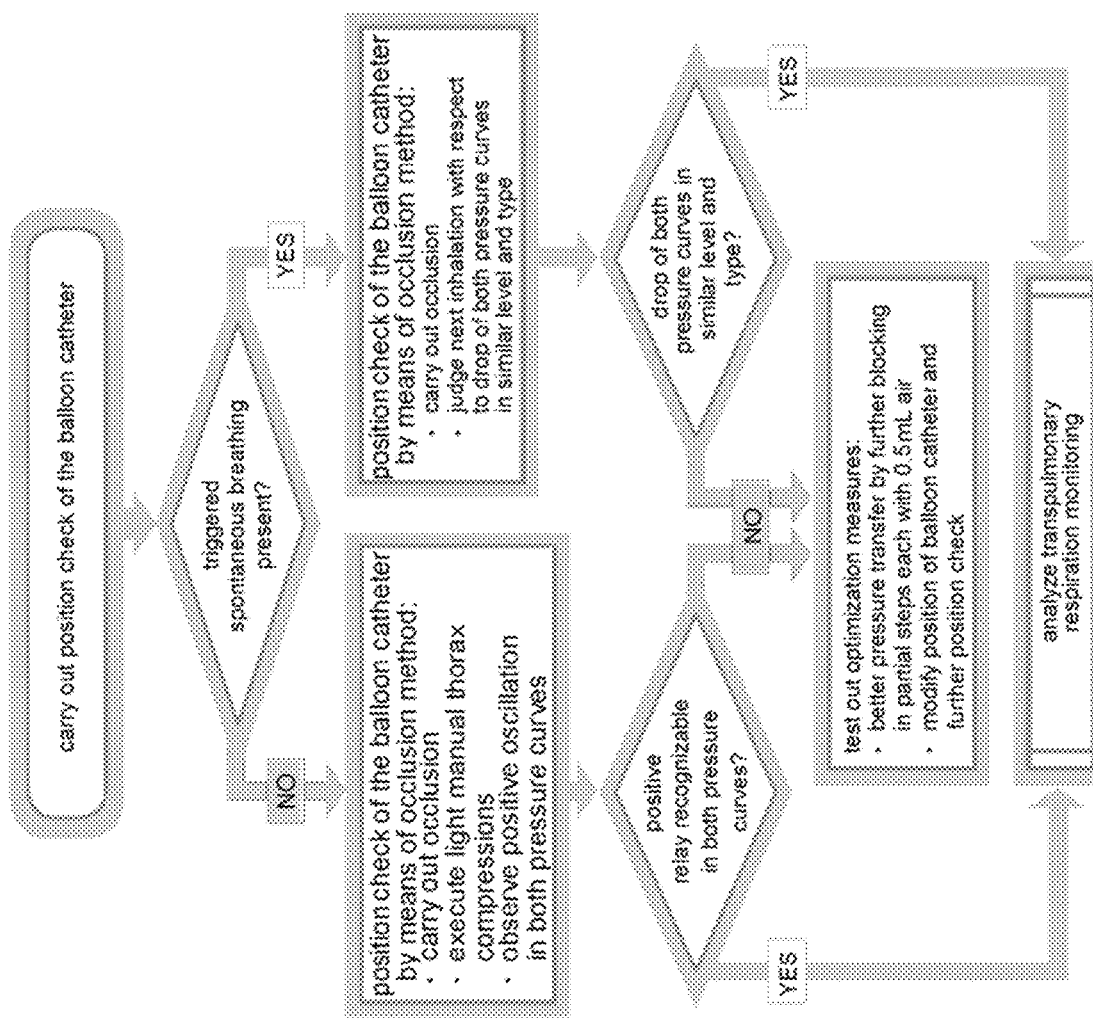
FIG. 6 shows the position check of the Peso catheter.

FIG. 6 shows the position check of the Peso catheter. After emptying, the esophageal balloon is secured using a three-way valve and a suitable lubricant is applied along the guide wire.

Comparably to a stomach tube, the Peso catheter is cautiously advanced up to a depth of approximately 55 cm down into the stomach and then filled using the minimum volume recommended by the producer. The intra-gastric catheter position is confirmed by a light external manual gastric compression, which induces a positive pressure deflection. Subsequently, the catheter is gradually drawn back into the esophagus.

Positioning in the esophagus is recognizable from the occurrence of cardiac artifacts in the pressure measurement and due to the change from intra-abdominal to intra-thoracic pressure curve patterns. Due to the placement of the esophageal balloon within the lower two-thirds of the intrathoracic esophagus, possible pressure artifacts because of the inhomogeneous compression of the esophagus due to external structures are supposed to be avoided. If spontaneous inspiratory efforts exist, the conventional test for validating the Peso measurement consists of comparing the simultaneous negative deflections of the airway pressure and esophageal pressure during an end-expiratory occlusion maneuver (so-called Baydur test). During the occluded inspiration, the pressure changes in the airway ($\Delta$Paw) and in the esophagus ($\Delta$Peso) are supposed to be almost identical, because the lung volume does not change and therefore a change also does not occur in the PL. The Peso measurement is considered to be reliable if the ratio $\Delta$Peso/$\Delta$Paw is between 0.8 and 1.2. Otherwise, the catheter has to be repositioned and/or the balloon volume has to be checked again.

In mandatorily respirated patients, an external manual thorax compression is to be applied during an expiratory pause (hold maneuver), during which the simultaneous positive deflections of the airway pressure and of the esophageal pressure are to be compared (overpressure occlusion test). With identical positioning of the Peso catheter, the Baydur test and the overpressure occlusion test supply similar pressure changes in the airways and in the esophagus. The absolute value can be substantially higher if the esophageal balloon is positioned in the lower third of the esophagus instead of in the middle third, because the superimposed pressure due to heart and lungs is higher here. Moreover, the pressure which is generated by the esophageal wall as a reaction to the balloon filling can increase the absolute value of the Peso above that of the pleural pressure. A calibration method according to the invention for remedying this artifact is that the use of the absolute value of the esophageal pressure is improved, in particular if balloons having large volume are used.

Optimizing the Respiration of Patients

The use of esophageal measurement as a basis of respiration therapy in ARDS patients is shown by way of example in an esophageal-pressure-controlled respiration.

The PEEP values are set with the goal of achieving a transpulmonary pressure (64) between 0 and 10 cm H2O in the end-expiratory phase according to a sliding scale based on the ratio PaO2/FIO2. The tidal volume is restricted to keep the transpulmonary pressure in the end-inspiratory phase below 25 cm H2O. The PEEP optimization can therefore be set on the basis of the Peso monitoring to minimize the occurrence of an atelectrauma, optimize the oxygenation, and improve the compliance of the respiratory system.

The end-expiratory transpulmonary pressure (64, TPP exsp) (=alveolar pressure (65)–pleural pressure (63)) can be adapted by the titration of the applied PEEP, since the airway pressure is related to the applied PEEP. The titration of the applied PEEP to an end-expiratory transpulmonary pressure between 0 and 10 mbar, but at least in the positive range, can reduce the cyclic alveolar collapse.

The end-inspiratory transpulmonary pressure TPP insp (plateau pressure–pleural pressure) can reduce the alveolar overstretching and thus assist the optimization of the set tidal volume and/or the inspiration pressure. A range of up to 20 mbar is the target range, depending on the clinical findings.

TABLE 2

PEEP optimization and avoidance of overstretching of lung areas

| Abbreviation | Definition | Clinical significance | Clinical recommendation |
|---|---|---|---|
| (64) TPP exp. | End-expiratory transpulmonary pressure (PEEP − Peso) | Breath cycle alveolar collapse | In the positive range |
| (64) TPP insp. | End-inspiratory transpulmonary pressure (plateau pressure − Peso) | Alveolar overstretching | <25 mbar |
| ΔPESO | Driving Pressure esophagus (ΔPeso = VT/Compliance) | Independent mortality factor | <12 mbar |
| ΔTPP | Transpulmonary Driving Pressure (TPP exp − TPP insp) | Measure of the tidal stress of the lung parenchyma Ratio of tidal volume to (static) respiratory compliance | <12 mbar |

The Weaning Process Under Peso Monitoring

The measurement of the breathing work to quantify the breathing effort enables Peso measurements to adapt the degree of the muscle relief while breathing individually to the patient. In this way, an increased breathing muscle exertion with the hazard of respiratory exhaustion can be recognized and as a result the risk of a weaning failure can be minimized. In this case, the inspiration breathing work can be determined both as the area integral over time (PTP=pressure-time product) and also over the volume (WOB=work of breathing). Both measuring methods are effective methods for estimating the power loss or the power consumption of the breathing musculature. The work is expressed as force×displacement. In a spontaneously breathing patient, the work performed by the breathing muscles is equal to the integral of the product of Pmus and volume change. If volume is generated, there is normally a close correlation between WOB and PTP.

The WOB per breathing cycle is normally expressed in joules. Work per minute is computed by multiplying WOB per cycle by the corresponding breath rate. Work per liter is computed by dividing work per minute by minute volume. One joule is the work which is required to move 1000 mL of tidal volume over a pressure difference of 10 cm H2O. An orienting normal value range can be defined by these definitions.

Multiple studies have shown that the breathing effort increases if patients fail in a weaning attempt. In the course of one study for spontaneous breathing, the PTP remained unchanged upon the successful weaning of patients. In contrast, patients having failed weaning as a result of an increase of the mechanical strain of the breathing musculature developed a clear and progressive increase of PTP. At the end of the study, the PTP of the unweaned patients increased by more than four times the normal value. In the course of a failed weaning attempt, Peso variations had greater changes than the Rapid Shallow Breathing Index (RSBI).

New approaches result with the differentiation of resistive and elastic breathing work, to orient the type of the assisted respiration selectively so that the breathing work is reduced.

TABLE 3

Weaning

| Abbreviation | Definition | Clinical significance | Clinical recommendation |
|---|---|---|---|
| WOB | Work of Breathing: measure of the inspiration breathing work per breath area integral over the volume | Risk of respiratory exhaustion | 0.3-0.6 Joule/liter |
| WOB/min | Measure of the inspiration breathing work per minute (integral over the volume) transferred to the breath minute volume | Risk of respiratory exhaustion | 2.4 joules per minute |
| PTPes | Pressure Time Product: measure of the breathing effort of the breathing musculature area integral over time (=pressure-time product) | Risk of respiratory exhaustion | >150 cmH2O*s |

Measurement of the Functional or Intrinsic PEEP

In chronic obstructive pulmonary diseases, obstructions can occur in the small airways. The incomplete exhalation accompanying this of the inhaled breath volume results in a consequential overinflation of the lungs ("intrinsic PEEP"). In a similar manner, a comparable problem can also be caused by an inadequate setting of the exhalation time. The lung volume which is not breathed out generates a functional positive end-expiratory pressure, which is referred to as intrinsic PEEP (PEEPi). The level of the PEEPi is a valid indicator of the dynamic overinflation of the COPD lung.

The respective intrinsic PEEP has to be overcome by the inspiration musculature during each inhalation by corresponding pleural pressure negation, before an inspiration respiratory gas flow occurs. The breathing work required for this purpose is referred to as "isometric breathing work" and can make up more than half of the total breathing work depending on the severity of the COPD.

TABLE 4

Spontaneous breathing

| Abbreviation | Definition | Clinical significance | Clinical recommendation |
|---|---|---|---|
| Peso min | Lowest pressure within a breathing cycle | Measure of inadequate spontaneous breathing (for example in ARDS) | relative < 10 mbar |
| Δ PEEP/ Peso min | Pressure delta between PEEP and Peso min in the inspiration | Measure of inadequate spontaneous breathing (for example in ARDS) | <10 mbar |

In contrast to the PEEPi measurement by means of a special maneuver of the respirator, with spontaneous breathing, the intrinsic PEEP can be measured progressively with correctly located Peso catheter. In this case, the flow-inactive drop of the esophageal pressure during the inspiration is measured, which is a surrogate parameter for the PEEPi. The trapping volume can be calculated building thereon.

According to the invention, the optimum PEEP can also be found by determining the transpulmonary pressure. The transpulmonary pressure is determined as the difference between alveolar pressure and pleural pressure, wherein the pleural pressure is estimated by measuring the Peso pressure (60). According to the invention, an alveolar collapse in the expiration is only prevented with positive end-expiratory transpulmonary pressure. The pressure control is accordingly carried out in such a way that a positive transpulmonary pressure prevails at end-expiratory.

TABLE 5

Inadequate expiration

| Abbreviation | Definition | Clinical significance | Clinical recommendation |
|---|---|---|---|
| PEEPi | Intrinsic PEEP | Measure of the dynamic PEEP (Auto-PEEP) | Monitoring & possibly adaptation: inspiration time expiration time frequency pressure increase speed ("ramp") inspirational termination ("flow shutdown criterion", for example PSV end flow") PEEP level of the pressure assistance |
| Vtrap | Trapping volume | Indicator of alveolar overstretching ("overinflation") | Monitoring & possibly adaptation: inspiration time expiration time frequency pressure increase speed ("ramp") inspirational termination ("flow shutdown criterion", for example PSV end flow") PEEP level of the pressure assistance |

FIG. 7 illustrates the determination of a failed trigger rate. The system moreover has a unit for recording the synchronicity (28) of a respiratory gas stroke (47) (pressure or volume or flow) chronologically specified by the respirator (20) with the breathing effort (41) of the patient (40). The unit for detecting the synchronicity (28) can be part of the control unit (19).

The number of inspiration efforts (41) of the patient (per unit of time) is recognized and recorded from the esophageal pressure curve (60).

From the respiration pressure curve (27) or corresponding to the specified values of the control unit (with monitored respiration), the number of specified inspirations (47) (per unit of time) is recognized or inferred and recorded.

The inspiration efforts of the patient (41) (per unit of time) are compared to the specified inspirations (47) (per unit of time) and the degree of the synchronization (30) between the inspiration efforts (41) of the patient and the inspiration specification (47) of the respirator is thus determined.

An index (31) of the failed triggers can be inferred from this comparison, which index represents the degree of the synchronization (30) between the inspiration efforts of the patient and the inspiration specification of the respirator. The index (31) and/or the degree of the synchronization (3) can be output, for example, on the display unit (3) of the respirator or on a monitor. The index (31) and/or the degree of the synchronization (30) can alternatively or additionally also be at least partially taken into consideration by the control unit (19) for the control of the respiration, for example, in monitored respiration, by the frequency of the breath strokes (47) being automatically adapted in consideration of index (31) and/or of the degree of the synchronization (30).

The respirator or a monitor has a unit for recording the synchronicity (28), which can be embodied as part of the control unit (19), which recognizes failed triggers (31) from the time interval (29) between the specified respiratory gas stroke (47) and the breathing effort (41) of the patient (40) and determines and stores or displays a failed trigger rate or an index (31).

The unit for recording the synchronicity (28) determines failed triggers (31) from the time interval between the specified respiratory gas stroke (47) and the breathing effort (41) of the patient if the time interval (29) is greater than $\frac{1}{100}$ of a second, preferably greater than $\frac{1}{10}$ of a second, particularly preferably greater than 1 second.

What is claimed is:

1. A system for recording breathing efforts of a patient, wherein the system comprises a pressure determination device for determining a pressure at a point in time of a breathing effort of the patient, the pressure determination device being designed as an esophageal catheter with a single gas-filled balloon, the system further comprising a respirator which comprises a pressure inlet nozzle for the esophageal catheter and a pressure sensor, wherein a breathing effort of the patient is recorded via the gas-filled balloon of the esophageal catheter, the system further comprising a unit which is configured to compare a respiratory gas stroke in the form of respiratory pressure or respiratory volume or respiratory flow which is chronologically specified by the respirator with the breathing effort of the patient for determining a synchronicity, and wherein an index of failed triggers is inferred from the comparison, where the index represents a degree of synchronization between the inspiration efforts of the patient and the inspiration specification of the respirator.

2. The system of claim 1, wherein the unit generates a control signal for the respirator to specify a changed inhalation time and/or a changed positive end-expiratory pressure (PEEP) and/or a changed trigger sensitivity if failed triggers are recognized.

3. The system of claim 1, wherein the esophageal catheter is used to determine the functional positive end-expiratory pressure, referred to as intrinsic PEEP (PEEPi).

4. The system of claim 3, wherein, if the PEEPi exceeds or falls below a threshold value, the unit generates a control signal for the respirator to specify a changed respiratory gas volume or a changed exhalation time.

5. The system of claim 1, wherein the sensor of the respirator determines the esophageal pressure, which is recorded via the gas-filled balloon of the esophageal catheter.

6. The system of claim 1, wherein a transpulmonary pressure is determined by the respirator based on the respiration pressure specified by the respirator and the esophageal pressure determined by the sensor.

7. The system of claim 1, wherein a determination of a transpulmonary pressure is performed at an end of an exhalation (TPP ex) and/or at an end of an inhalation (TPP in) by a specific measuring procedure, in which the respirator prevents a respiratory gas transportation to or from the patient.

8. The system of claim 1, wherein a breathing effort of the patient is compared to at least one stored threshold value and corresponds to a trigger if the breathing effort exceeds the threshold value.

9. The system of claim 1, wherein the point in time is a beginning of an expiration or a beginning of an inspiration of the patient.

10. The system of claim 1, wherein the pressure determination device determines the esophageal pressure continuously.

11. The system of claim 1, wherein the system further comprises a unit which specifies the respiratory gas pressure provided by the respirator based on a determined esophageal pressure or a determined transpulmonary pressure.

12. The system of claim 11, wherein if the esophageal pressure exceeds or falls below a threshold value, the unit generates a control signal for the respirator to specify an inspiratory or expiratory respiratory gas pressure.

13. The system of claim 1, wherein a number of inspiration efforts of the patient per time unit is recognized and recorded from an esophageal pressure curve and/or a number of specified inspirations per time unit is recognized and recorded from a respiration pressure curve or the control unit.

14. The system of claim 13, wherein the inspiration efforts of the patient per time unit are compared to the specified inspirations per time unit and the degree of synchronization between the inspiration efforts of the patient and the inspiration specification of the respirator is thus determined.

15. The system of claim 14, wherein an index of failed triggers is inferred from the comparison, which index represents the degree of synchronization between the inspiration efforts of the patient and the inspiration specification of the respirator.

16. The system of claim 15, wherein the unit for recording a synchronicity recognizes failed triggers from a time interval between the specified respiratory gas stroke and the respiratory effort of the patient and determines and stores or displays a failed trigger rate or an index.

17. The system of claim 16, wherein the unit for recording a synchronicity from a time interval between a specified respiratory gas stroke and a respiratory effort of the patient recognizes failed triggers if the time interval is greater than a 1/10 of a second.

18. The system of claim 16, wherein the unit for recording a synchronicity from a time interval between a specified respiratory gas stroke and a respiratory effort of the patient recognizes failed triggers if the time interval is greater than a second.

19. The system of claim 1, wherein the system further comprises a unit for recording an optimum filling volume of the balloon, the unit determining the smallest filling volume which causes the greatest pulse pressure variation of the balloon in a breath from inspiration to expiration.

20. The system of claim 1, wherein the system further comprises a unit for recording an optimum filling volume of the balloon, the unit determining the filling volume which causes the greatest pulse pressure variation of the balloon in one breath from inspiration to expiration.

* * * * *